United States Patent
Mohanasundaram et al.

(10) Patent No.: US 11,219,457 B2
(45) Date of Patent: Jan. 11, 2022

(54) LAPAROSCOPIC PURSE STRING SUTURE DEVICE

(71) Applicant: Covidien LP, Mansfield, MA (US)

(72) Inventors: Suresh Kumar Prema Mohanasundaram, Chennai (IN); Avvln Srinivasa Murthy Aravalli, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 232 days.

(21) Appl. No.: 16/532,903

(22) Filed: Aug. 6, 2019

(65) Prior Publication Data

US 2020/0113564 A1 Apr. 16, 2020

Related U.S. Application Data

(60) Provisional application No. 62/744,147, filed on Oct. 11, 2018.

(51) Int. Cl.
*A61B 17/11* (2006.01)
*A61B 17/04* (2006.01)
(Continued)

(52) U.S. Cl.
CPC .......... *A61B 17/11* (2013.01); *A61B 17/0469* (2013.01); *A61B 17/295* (2013.01);
(Continued)

(58) Field of Classification Search
CPC ..... A61B 17/3201; A61B 34/70; A61B 46/10; A61B 17/28; A61B 17/30; A61B 2017/00477; A61B 90/50
See application file for complete search history.

(56) References Cited

U.S. PATENT DOCUMENTS 1,822,330 A 9/1931 Ainslie
2,327,353 A 8/1943 Karie
(Continued)

FOREIGN PATENT DOCUMENTS

CN 203564286 U 4/2014
EP 0647431 A2 4/1995
(Continued)

OTHER PUBLICATIONS

European Office Action dated Feb. 21, 2020 corresponding to counterpart Patent Application EP 19202437.0.
(Continued)

*Primary Examiner* — Julian W Woo (57) ABSTRACT

A surgical suturing apparatus includes an end effector including a jaw assembly and a needle assembly. The jaw assembly includes first and second jaws movable between open and closed positions. Each of the first and second jaws includes a tissue facing surface having an elongated rail and a longitudinal row of teeth. Each tooth of the longitudinal rows of teeth of the first and second jaws includes a needle channel extending therethrough. The elongated rails and the longitudinal rows of teeth of the first and second jaws are disposed in opposed relation relative to each other. The needle assembly includes a first needle, a second needle, and a suture coupled to the first and second needles. The first needle is slidable through the needle channels of the first jaw and the second needle is slidable through the needle channels of the second jaw.

20 Claims, 8 Drawing Sheets

(51) Int. Cl.
*A61B 17/295* (2006.01)
*A61B 17/06* (2006.01)

(52) U.S. Cl.
CPC .............. *A61B 2017/0472* (2013.01); *A61B 2017/06057* (2013.01); *A61B 2017/1103* (2013.01); *A61B 2017/1125* (2013.01)

(56) References Cited

U.S. PATENT DOCUMENTS

| | | | |
|---|---|---|---|
| 3,073,311 A | 1/1963 | Tibbs et al. | |
| 4,236,470 A | 12/1980 | Stenson | |
| 4,345,600 A * | 8/1982 | Rothfuss | A61B 17/04 606/148 |
| 4,915,107 A * | 4/1990 | Rebuffat | A61B 17/0469 606/144 |
| 5,037,433 A | 8/1991 | Wilk et al. | |
| 5,042,707 A | 8/1991 | Taheri | |
| 5,100,430 A | 3/1992 | Avellanet et al. | |
| 5,188,636 A | 2/1993 | Fedotov | |
| 5,209,747 A | 5/1993 | Knoepfler | |
| 5,300,082 A | 4/1994 | Sharpe et al. | |
| 5,308,353 A | 5/1994 | Beurrier | |
| 5,314,445 A | 5/1994 | Heidmueller nee Degwitz et al. | |
| 5,330,502 A | 7/1994 | Hassler et al. | |
| 5,350,391 A | 9/1994 | Iacovelli | |
| 5,374,277 A | 12/1994 | Hassler | |
| 5,389,103 A | 2/1995 | Melzer et al. | |
| 5,403,342 A | 4/1995 | Tovey et al. | |
| 5,411,481 A * | 5/1995 | Allen | A61B 17/1114 606/144 |
| 5,425,737 A * | 6/1995 | Burbank | A61B 17/0469 606/139 |
| 5,439,478 A | 8/1995 | Palmer | |
| 5,454,822 A | 10/1995 | Schob et al. | |
| 5,454,823 A | 10/1995 | Richardson et al. | |
| 5,454,827 A | 10/1995 | Aust et al. | |
| 5,480,406 A | 1/1996 | Nolan et al. | |
| 5,540,706 A | 7/1996 | Aust et al. | |
| 5,564,615 A | 10/1996 | Bishop et al. | |
| 5,575,799 A | 11/1996 | Bolanos et al. | |
| 5,582,617 A | 12/1996 | Klieman et al. | |
| 5,591,181 A | 1/1997 | Stone et al. | |
| 5,601,224 A | 2/1997 | Bishop et al. | |
| 5,620,415 A | 4/1997 | Lucey et al. | |
| 5,643,294 A | 7/1997 | Tovey et al. | |
| 5,649,938 A * | 7/1997 | Allen | A61B 17/1114 606/144 |
| 5,674,229 A | 10/1997 | Tovey et al. | |
| 5,690,652 A | 11/1997 | Wurster et al. | |
| 5,690,653 A | 11/1997 | Richardson et al. | |
| 5,752,973 A | 5/1998 | Kieturakis | |
| 5,759,188 A | 6/1998 | Yoon | |
| 5,766,196 A | 6/1998 | Griffiths | |
| 5,779,646 A | 7/1998 | Koblish et al. | |
| 5,792,165 A | 8/1998 | Klieman et al. | |
| 5,797,537 A | 8/1998 | Oberlin et al. | |
| 5,797,927 A | 8/1998 | Yoon | |
| 5,814,054 A | 9/1998 | Kortenbach et al. | |
| 5,817,119 A | 10/1998 | Klieman et al. | |
| 5,827,323 A | 10/1998 | Klieman et al. | |
| 5,865,836 A | 2/1999 | Miller | |
| 5,876,412 A | 3/1999 | Piraka | |
| 5,897,563 A | 4/1999 | Yoon et al. | |
| 5,906,630 A | 5/1999 | Anderhub et al. | |
| 5,908,428 A | 6/1999 | Scirica et al. | |
| 5,928,136 A | 7/1999 | Barry | |
| 5,954,731 A | 9/1999 | Yoon | |
| 5,954,733 A | 9/1999 | Yoon | |
| 5,957,937 A | 9/1999 | Yoon | |
| 5,984,932 A | 11/1999 | Yoon | |
| 5,993,466 A | 11/1999 | Yoon | |
| 5,993,467 A | 11/1999 | Yoon | |
| 5,997,565 A | 12/1999 | Inoue | |
| 6,004,332 A | 12/1999 | Yoon et al. | |
| 6,017,358 A | 1/2000 | Yoon et al. | |
| 6,027,522 A | 2/2000 | Palmer | |
| 6,077,287 A | 6/2000 | Taylor et al. | |
| 6,080,180 A | 6/2000 | Yoon et al. | |
| 6,086,601 A | 7/2000 | Yoon | |
| 6,126,665 A | 10/2000 | Yoon | |
| 6,139,563 A | 10/2000 | Cosgrove, III et al. | |
| 6,143,005 A | 11/2000 | Yoon et al. | |
| 6,171,316 B1 | 1/2001 | Kovac et al. | |
| 6,206,893 B1 | 3/2001 | Klein et al. | |
| 6,214,028 B1 | 4/2001 | Yoon et al. | |
| 6,223,100 B1 | 4/2001 | Green | |
| 6,224,614 B1 | 5/2001 | Yoon | |
| 6,241,139 B1 | 6/2001 | Milliman et al. | |
| 6,261,307 B1 | 7/2001 | Yoon et al. | |
| 6,319,262 B1 | 11/2001 | Bates et al. | |
| 6,330,965 B1 | 12/2001 | Milliman et al. | |
| 6,358,259 B1 | 3/2002 | Swain et al. | |
| 6,494,888 B1 | 12/2002 | Laufer et al. | |
| 6,506,196 B1 | 1/2003 | Laufer | |
| 6,517,539 B1 | 2/2003 | Smith et al. | |
| 6,569,105 B1 | 5/2003 | Kortenbach et al. | |
| 6,582,450 B2 | 6/2003 | Ouchi | |
| 6,638,287 B2 | 10/2003 | Danitz et al. | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,676,676 B2 | 1/2004 | Danitz et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,773,441 B1 | 8/2004 | Laufer et al. | |
| 6,821,285 B2 | 11/2004 | Laufer et al. | |
| 6,835,200 B2 | 12/2004 | Laufer et al. | |
| 6,889,116 B2 | 5/2005 | Jinno | |
| 6,936,061 B2 | 8/2005 | Sasaki | |
| 6,972,017 B2 | 12/2005 | Smith et al. | |
| 6,981,628 B2 | 1/2006 | Wales | |
| 6,997,931 B2 | 2/2006 | Sauer et al. | |
| 7,052,489 B2 | 5/2006 | Griego et al. | |
| RE39,152 E | 6/2006 | Aust et al. | |
| 7,063,715 B2 | 6/2006 | Onuki et al. | |
| 7,107,124 B2 | 9/2006 | Green | |
| 7,128,253 B2 | 10/2006 | Mastri et al. | |
| 7,153,314 B2 | 12/2006 | Laufer et al. | |
| 7,248,944 B2 | 7/2007 | Green | |
| 7,819,896 B2 | 10/2010 | Racenet | |
| 8,931,679 B2 | 1/2015 | Kostrzewski | |
| 9,271,723 B2 | 3/2016 | Taylor et al. | |
| 2004/0010245 A1 | 1/2004 | Cerier et al. | |
| 2004/0060410 A1 | 4/2004 | Leung et al. | |
| 2005/0256533 A1 | 11/2005 | Roth et al. | |
| 2006/0111732 A1 | 5/2006 | Gibbens et al. | |
| 2006/0253126 A1 | 11/2006 | Bjerken et al. | |
| 2006/0282093 A1 | 12/2006 | Shelton, IV et al. | |
| 2007/0005110 A1 | 1/2007 | Collier et al. | |
| 2009/0259233 A1 | 10/2009 | Bogart et al. | |
| 2015/0157320 A1 | 6/2015 | Zergiebel et al. | |
| 2015/0157321 A1 | 6/2015 | Zergiebel et al. | |

FOREIGN PATENT DOCUMENTS

| | | |
|---|---|---|
| EP | 3097864 A2 | 11/2016 |
| JP | 6382570 B2 | 8/2018 |
| WO | 9811829 A1 | 3/1998 |
| WO | 0174254 A1 | 10/2001 |
| WO | 03017850 A2 | 3/2003 |
| WO | 03028541 A2 | 4/2003 |
| WO | 2006061868 A1 | 6/2006 |
| WO | 2009132284 A2 | 10/2009 |

OTHER PUBLICATIONS

Extended European Search Report dated Feb. 21, 2020 corresponding to counterpart Patent Application EP 19202437.0.

* cited by examiner

LAPAROSCOPIC PURSE STRING SUTURE DEVICE

CROSS-REFERENCE TO RELATED APPLICATION

This application claims the benefit of and priority to U.S. Provisional Patent Application No. 62/744,147 filed Oct. 11, 2018, the entire disclosure of which is incorporated by reference herein.

BACKGROUND

Technical Field

The present disclosure relates to surgical devices and methods of using the same. More particularly, the present disclosure relates to endoscopic surgical devices for affixing purse string sutures to tissue.

Description of Related Art

Surgical stapling apparatus are employed by surgeons to sequentially or simultaneously apply one or more rows of fasteners, e.g., staples or two-part fasteners, to body tissue for the purpose of joining segments of body tissue together and/or creating anastomoses.

Annular surgical stapling apparatus generally include a staple cartridge assembly including annular rows of staples, an anvil assembly operatively associated with the staple cartridge assembly, and an annular blade disposed internal to the annular rows of staples. In use, during an end-to-end circular anastomosis procedure, two ends of hollow tissue sections (e.g., bowels, intestines, or other tubular organs) are positioned between the anvil and staple cartridge assemblies and are joined by clamping the two ends together and driving the annular rows of staples through the clamped tissue sections. During firing of the staples, the annular blade is advanced to cut portions of the tissue sections extending inside the staple lines, thereby establishing a passage through the two stapled tissue sections.

The ends of the tissue sections may be secured over the anvil and staple cartridge assemblies by purse string sutures prior to approximating the anvil assembly relative to the staple cartridge assembly. Purse string sutures are utilized to close or narrow the openings or passages of the tissue sections. A suture is typically passed through the tissue section as a running stitch, in and out around the end of the tissue section, using a needle, staples, and/or an extracorporeal device for attaching the suture to tissue. After the tissue is stitched, the ends of the suture are brought together and pulled tight to close or narrow the opening in the tissue section. The ends of the suture may then be tied together.

For example, in laparascopic gastrointestinal end-to-end anastomosis, a surgeon may create an external incision to bring a target tissue section (e.g., intestine or colon) outside of the body, and attach a purse string suture to the tissue section using an extracorporeal device. Such a procedure, however, may cause complications, like bleeding, injury, or increased surgical and/or recovery time.

SUMMARY

The present disclosure is directed to a surgical device for placing purse string sutures in tissue within the body (e.g., intra-peritoneal space) without creating an external incision or using staples.

According to an aspect of the present disclosure, a surgical suturing device includes an end effector including a jaw assembly and a needle assembly. The jaw assembly includes first and second jaws movable between an open position and a closed position. Each of the first and second jaws includes a tissue facing surface having an elongated rail and a longitudinal row of teeth. Each tooth of the longitudinal rows of teeth of the first and second jaws includes a needle channel extending therethrough. The elongated rails and the longitudinal rows of teeth of the first and second jaws are disposed in opposed relation relative to each other. The needle assembly includes a first needle, a second needle, and a suture coupled to the first and second needles. The first needle is slidable through the needle channels of the longitudinal row of teeth of the first jaw and the second needle is slidable through the needle channels of the longitudinal row of teeth of the second jaw.

Each of the tissue facing surfaces of the first and second jaws may include a central longitudinal slot defined therein. The elongate rail and the longitudinal row of teeth of each of the first and second jaws may be disposed on opposed sides of the central longitudinal slot of the respective first or second jaw.

Each of the elongated rails of the first and second jaws may include a tissue clamping surface. The tissue clamping surfaces may be configured to grasp tissue therebetween when the jaw assembly is in the closed position. Each tooth of the longitudinal rows of teeth of the first and second jaws may include a tissue engaging surface. The tissue engaging surfaces may be configured to grasp tissue therebetween when the jaw assembly is in the closed position. Each tooth of the longitudinal rows of teeth of the first and second jaws may have a slit defined therein that extends between the needle channel and an outer surface of the tooth.

The first jaw may include a tip portion having first and second apertures extending therethrough. The first aperture may be aligned with the needle channels of the first jaw and the second aperture may be aligned with the needle channels of the second jaw when the jaw assembly is disposed in the closed position. Each of the first and second apertures of the tip portion may be defined by a semi-continuous surface such that the first and second apertures are open at an outer side surface of the tip portion.

Each of the first and second needles of the needle assembly may include a distal tip portion having a transverse hole extending therethrough. A first end portion of the suture may extend through the transverse hole of the first needle and a second end portion of the suture may extend through the transverse hole of the second needle. Each of the first and second needles may include a passageway extending between the transverse hole and an outer surface of the respective first or second needle.

The end effector may further include a proximal body portion and a mounting assembly pivotably coupling the proximal body portion to the jaw assembly. The mounting assembly may include first and second openings extending longitudinally therethrough that are aligned with the needle channels of the first and second jaws when the first and second jaws are in the closed position. The first and second openings may be configured for passage of the first and second needles therethrough.

The end effector may further include a drive assembly including an elongated drive beam and a knife. The knife may be movable through the central longitudinal slots of the first and second jaws.

The surgical suturing device may further include a handle assembly and an elongate body extending distally from the handle assembly. The end effector may extend distally from the elongate body portion.

According to another aspect of the present disclosure, a method of securing a purse string suture to tissue includes: positioning tissue between tissue facing surfaces of first and second jaws of an end effector of a surgical suturing device, each of the tissue facing surfaces of the first and second jaws including an elongated rail and a longitudinal row of teeth, each tooth of the longitudinal rows of teeth including a needle channel extending therethrough; closing the first and second jaws such that the tissue is clamped between the elongated rails of the first and second jaws and takes on a wave-like configuration between the longitudinal rows of teeth, the wave-like configuration including first tissue portions compressed together between opposed teeth of the longitudinal rows of teeth and second tissue portions spread apart and bowed into the spaces defined between adjacent teeth of each of the longitudinal rows of teeth; and actuating the surgical suturing device to advance a needle assembly of the end effector distally through the jaw assembly to suture the tissue disposed therebetween, the needle assembly including a suture coupled to first and second needles, the first and second needles slidable through the needle channels of the longitudinal rows of teeth of the first and second jaws and the tissue disposed in the spaces between adjacent teeth of the longitudinal rows of teeth.

Actuating the surgical suturing device may further include advancing a drive assembly of the end effector distally through the jaw assembly to cut the tissue disposed between the first and second jaws.

Actuating the surgical suturing device may include advancing distal tip portions of the first and second needles through first and second apertures defined in a tip portion of the first jaw. The method may further include grasping first and second end portions of the suture with grasping instruments. The method may further include retracting the needle assembly proximally into a proximal body portion of the end effector and opening the first and second jaws such that the suture passes through slits defined in each tooth of the longitudinal rows of teeth as well as an open side of the tip portion, leaving the suture attached to the tissue around a perimeter thereof.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein.

DETAILED DESCRIPTION OF THE EMBODIMENTS

Various exemplary embodiments of the present disclosure are discussed herein below in terms of surgical devices for securing sutures to tissue. The surgical devices described herein may be used to apply a suture to a hollow or tubular tissue section (also referred to herein, generally, as tissue) by grasping an end portion of the tissue between first and second jaws of the surgical device in a wave-like configuration and passing the suture therethrough.

Embodiments of the presently disclosed surgical suturing devices will now be described in detail with reference to the drawing figures wherein like reference numerals identify similar or identical elements. Throughout this description, the term "proximal" refers to a portion of a device, or component thereof, that is closer to a user, and the term "distal" refers to a portion of the device, or component thereof, that is farther from the user. Directional reference terms, such as "upper," "lower," "top," "bottom," "side," and the like, are intended to ease description of the embodiments and are not intended to have any limiting effect on the ultimate orientation of a device or any parts thereof.

Figures 1, 2:
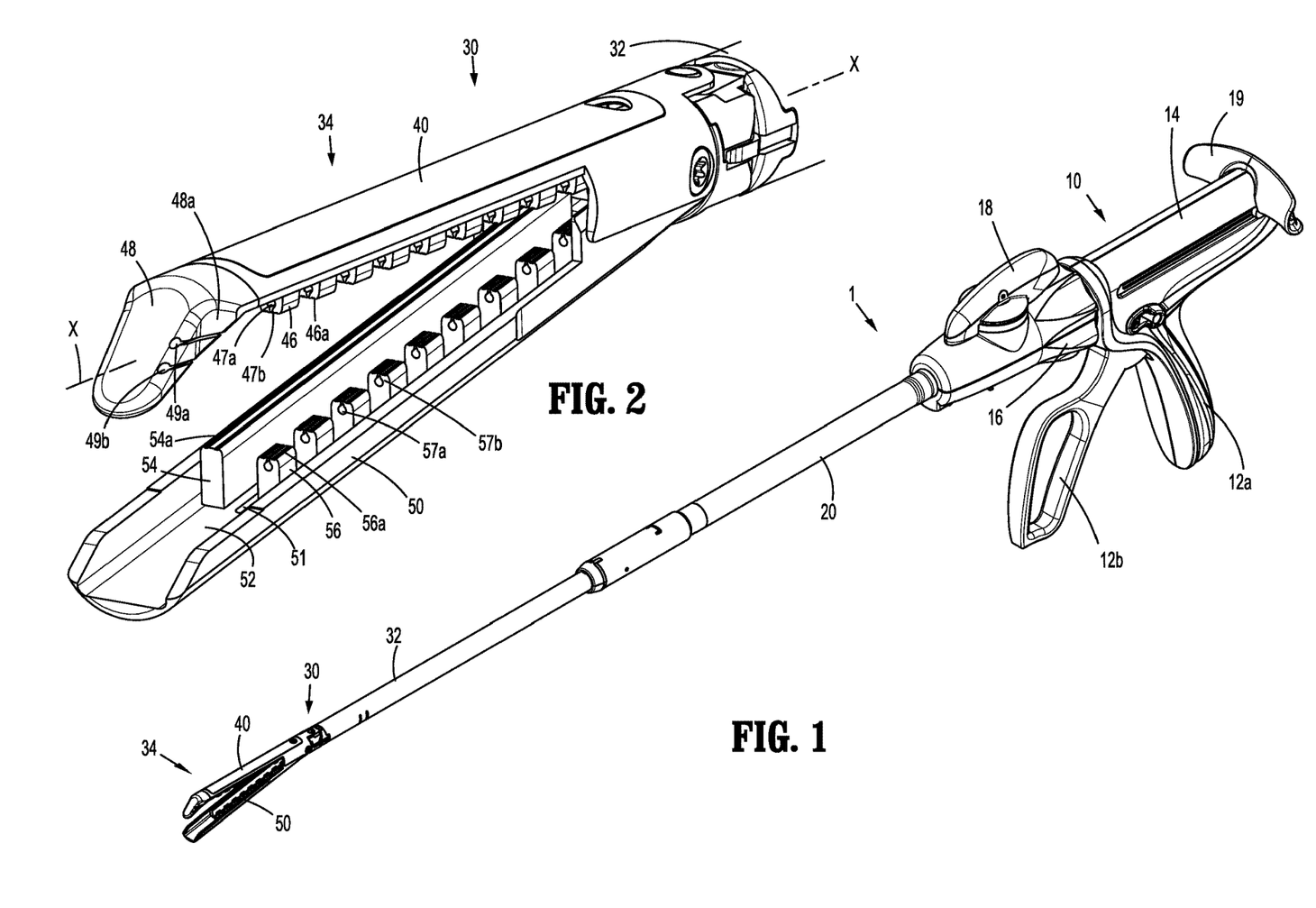
FIG. 1 is a side, perspective view of a surgical suturing device in accordance with an embodiment of the present disclosure.
FIGS. 2 and 3 are enlarged, perspective views of a jaw assembly of an end effector of the surgical suturing device of FIG. 1.

Referring now to FIG. 1, an exemplary surgical purse string suture device or surgical suturing device 1 is shown for applying purse string sutures to tissue. The surgical suturing device 1 generally includes a handle assembly 10, an elongate body portion 20 extending distally from the handle assembly 10, and an end effector 30 extending distally from the elongate body portion 20. The end effector 30 includes a proximal body portion 32 and a jaw assembly 34 pivotably attached to the proximal body portion 32. The end effector 30 may be releasably secured to the elongate body portion 20 such that the end effector 30 is replaceable with a new end effector 30, or the end effector 30 may be permanently affixed to the elongate body portion 20.

The jaw assembly 34 includes an upper or first jaw 40 and a lower or second jaw 50 disposed in opposed relation to the first jaw 40. The first jaw 40 and/or the second jaw 50 is pivotable with respect to the proximal body portion 32 of the end effector 30 such that the first and second jaws 40, 50 are movable between an open or unclamped position in which the first and second jaws 40, 50 are spaced apart with respect to each other (see e.g., FIG. 6) and a closed or clamped position in which the first and second jaws 40, 50 are substantially adjacent each other (see e.g., FIG. 7).

The handle assembly 10 includes a stationary handle portion 12a, a movable handle portion or trigger 12b, and a barrel portion 14. A rotatable member 16 is mounted on the forward end of the barrel portion 14 to facilitate rotation of the elongate body portion 20 and thus, the end effector 30 with respect to the handle assembly 10 so as to properly orient the jaw assembly 34 relative to tissue to be sutured. An articulation lever 18 is also mounted on the forward end of the barrel portion 14 to facilitate articulation of the jaw assembly 30. A retraction knob 19 is movably positionable along the barrel portion 14 to open and/or close the first and second jaws 40, 50, relative to each other. Actuation of the trigger 12b applies a purse string suture 66 (see e.g., FIG. 9A) to tissue captured between the first and second jaws 40, 50, as described in further detail below.

For a detailed description of the structure and function of exemplary handle assemblies or components thereof suitable for use in a surgical suturing device of the present disclosure, reference may be made to U.S. Pat. Nos. 6,330,965, 6,241,139, 7,819,896, 7,128,253, and 8,931,679, the entire contents of each of which are incorporated herein by reference.

Figure 3:
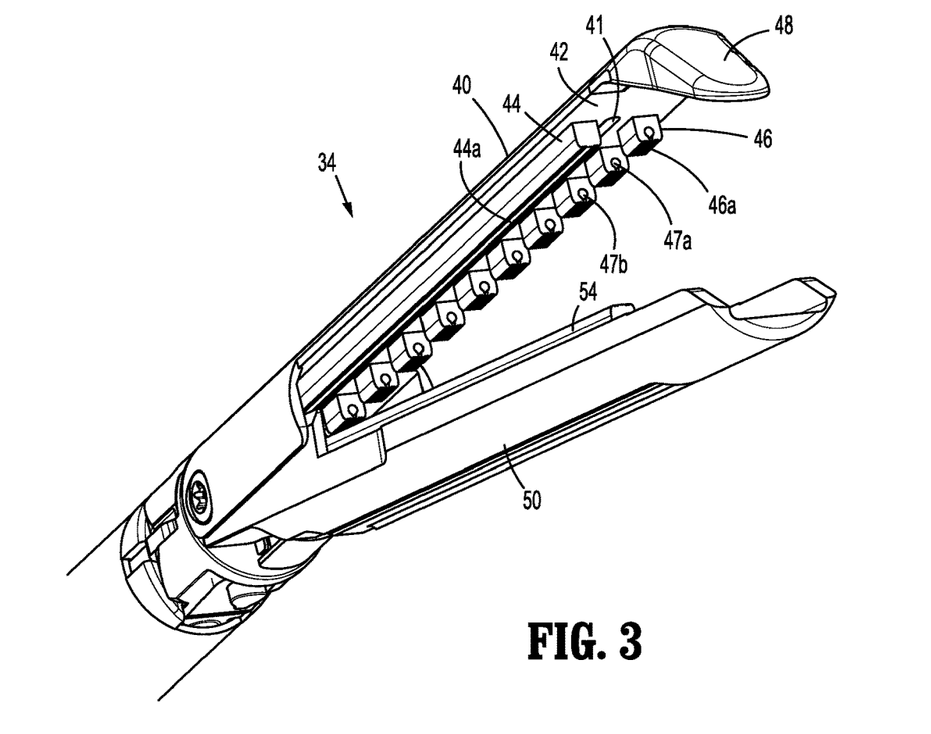

Turning now to FIGS. 2 and 3, the first jaw 40 of the jaw assembly 34 includes a tissue facing surface 42 having a central longitudinal slot 41 formed therein and extending along a central longitudinal axis "X" of the end effector 30. The first jaw 40 further includes an elongated rail 44 and a longitudinal row of teeth 46 extending outwardly from the tissue facing surface 42 towards the second jaw 50. The elongated rail 44 and the teeth 46 are disposed on opposed sides of the central longitudinal slot 41 in substantially parallel relation relative to one another. The elongated rail 44 and the teeth 46 extend longitudinally along the tissue facing surface 42 in laterally spaced relation relative to the central longitudinal slot 41 such that the elongated rail 44 and the teeth 46 are laterally offset from the central longitudinal axis "X" of the end effector 30.

The elongated rail 44 is a continuous uninterrupted block of biocompatible material having an outer or tissue clamping surface 44a. The tissue clamping surface 44a of the elongated rail 44 may be textured (e.g., grooved, roughened, etc.) to enhance the grip of the tissue clamping surface 44a to tissue. While the elongated rail 44 is shown as having a generally rectangular shape, it should be understood that the elongated rail 44 may be any shape, such as semi-circular shape, so long as the elongated rail 44 is dimensioned to grasp tissue between the first and second jaws 40, 50, as described in further detail below, when the jaw assembly 34 is moved to the closed position.

The teeth 46 are separate blocks of biocompatible material disposed in axially spaced relation relative to each other and each having an outer or tissue engaging surface 46a. The tissue engaging surface 46a may be textured (e.g., grooved, roughened, etc.) to enhance the grip of the tissue engaging surface 46a to tissue. Each tooth 46 includes a needle channel 47a defined therethrough, and a slit 47b extending between the needle channel 47a and the tissue engaging surface 46a. The needle channels 47a and the slits 47b of the teeth 46 are longitudinally aligned along the length of the first jaw 40. The needle channels 47a are sized and shaped for slidable movement of a needle therethrough, and the slits 47b are sized and shaped for passage of a suture therethrough.

While the teeth 46 are shown as having a generally square or rectangular shape, it should be understood that the teeth 46 may be any shape, such as cylindrical pegs, so long as the teeth 46 are arranged to allow for tissue disposed therebetween to take on a sinuous or wave-like configuration, as described in further detail below, when the jaw assembly 34 is moved to the closed position. Alternatively, the teeth 46 may be formed from one or more blocks of biocompatible material that are cut to include undulations (e.g., curves or steps) forming the teeth 46 and the spaces therebetween.

Figure 7:
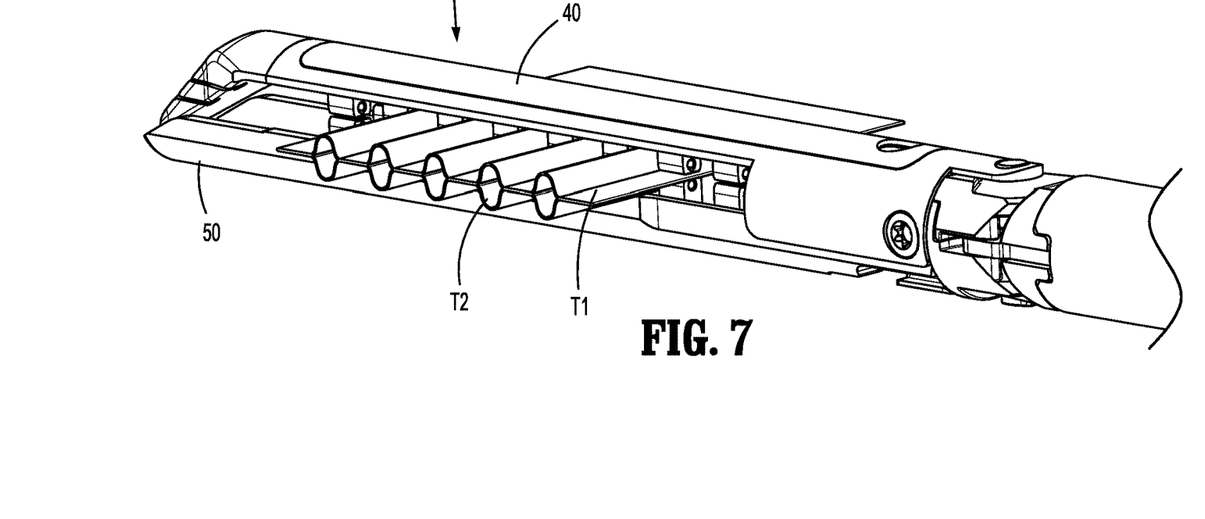
FIG. 7 is a side, perspective view of the jaw assembly of the end effector of FIG. 6, shown in a closed position with the tissue clamped between the first and second jaws.
Figure 10:
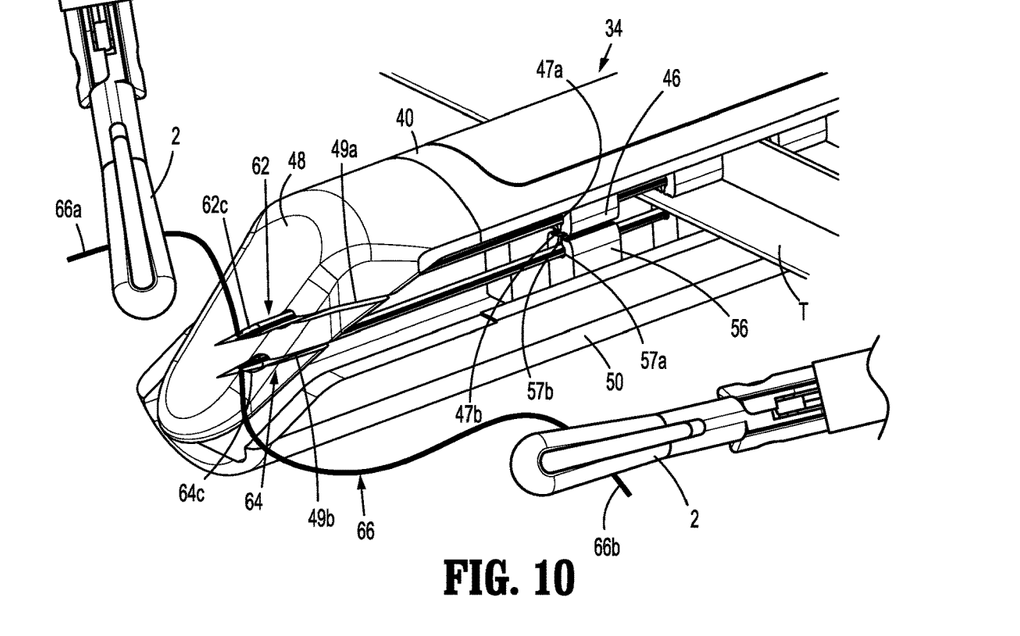
FIG. 10 is a side, perspective view of the end effector and the tissue of FIGS. 9A and 9B, at the end of the firing stroke of the surgical suturing device.

The first jaw 40 further includes a tip portion 48 at a distal end thereof. The tip portion 48 is curved to enhance visualization and/or maneuverability of the jaw assembly 34 around target tissue. The tip portion 48 of the first jaw 40 may aid in tissue manipulation, allowing for blunt dissection and/or mobilization. Other configurations of the tip portion 48 are envisioned depending upon, for example, the desired characteristics of the jaw assembly 34 as should be understood by those skilled in the art. When jaw assembly 34 is closed, as seen in FIGS. 7 and 10, the tip portion 48 of the first jaw 40 extends at least partially into or across the second jaw 50.

The tip portion 48 includes an upper or first aperture 49a and a lower or second aperture 49b defined therethrough. The first and second apertures 49a, 49b are longitudinally oriented and aligned with the needle channels 47a, 57a of the first and second jaws 40, 50, respectively. The first and second apertures 49a, 49b are configured for passage of needles longitudinally therethrough. As seen in FIG. 2, the first and second apertures 49a, 49b are defined by a semi-continuous surface having a generally c-shaped configuration and are open at an outer side surface 48a of the tip portion 48 to allow for passage of a suture, but not the needle, therethrough. The first aperture 49a of the tip portion 48 is axially aligned with or in registration with the needle channels 47a of the teeth 46 of the first jaw 40. Further, when the jaw assembly 34 is closed, as seen in FIGS. 7 and 10, the second aperture 49b of the tip portion 48 is axially aligned with or in registration with the needle channels 57a of the teeth 56 of the second jaw 50, as described in detail below.

With continued reference to FIG. 2, the second jaw 50 of the jaw assembly 34 includes a tissue facing surface 52 having a central longitudinal slot 51 formed therein, and an elongated rail 54 and a longitudinal row of teeth 56 extending outwardly from the tissue facing surface 52 towards the first jaw 40. The structure and relative positioning of the central longitudinal slot 51, the elongated rail 54, and the teeth 56 of the second jaw 50 are substantially the same as the central longitudinal slot 41, the elongate rail 44, and the teeth 46 of the first jaw 40.

Specifically, the central longitudinal slot 51 extends along the central longitudinal axis "X" of the end effector 30, and the elongated rail 44 and the teeth 46 are disposed on opposed sides of the central longitudinal slot 51 in substantially parallel relation relative to one another. The elongated rail 54 and the teeth 56 extend longitudinally along the tissue facing surface 52 in laterally spaced relation relative to the central longitudinal slot 51 such that the elongated rail 54 and the teeth 56 are laterally offset from the central longitudinal axis "X" of the end effector 30.

The elongated rail 54 is a continuous uninterrupted block of biocompatible material having an outer or tissue clamping surface 54a. The tissue clamping surface 54a of the elongated rail 54 may be textured (e.g., grooved, roughened, etc.) to enhance the grip of the tissue clamping surface 54a to tissue. The size and shape of the elongated rail 54 may vary, as discussed above with regard to the elongated rail 44 of the first jaw 40.

The teeth 56 are separate blocks of biocompatible material disposed in axially spaced relation relative to each other and each having an outer or tissue engaging surface 56a. The tissue engaging surface 56a may be textured (e.g., grooved, roughened, etc.) to enhance the grip of the tissue engaging surface 56a to tissue. Each tooth 56 includes a needle channel 57a defined therethrough, and a slit 57b extending between the needle channel 57a and the tissue engaging surface 56a. The needle channels 57a and the slits 57b of the teeth 56 are longitudinally aligned along the length of the second jaw 50. The needle channels 57a are sized and shaped to allow for slidable movement of a needle therethrough, and the slits 57b are sized and shaped to allow for passage of a suture therethrough. The size, shape, and/or formation of the teeth 56 may vary, as discussed above with regard to the teeth 46 of the first jaw 40.

The tissue facing surface 52 of the second jaw 50 is a mirror image of the tissue facing surface 42 of the first jaw 40. Accordingly, the tissue facing surfaces 42, 52 of the first and second jaws 40, 50 are disposed in opposed relation relative to each other such that the central longitudinal slot 41 of the first jaw 40 opposes and is aligned with the central longitudinal slot 51 of the second jaw 50, the elongated rail 44 of the first jaw 40 opposes and is aligned with the elongated rail 54 of the second jaw 50, and the teeth 46 of the first jaw 40 oppose and are aligned with the teeth 56 of the second jaw 50.

Figure 4:
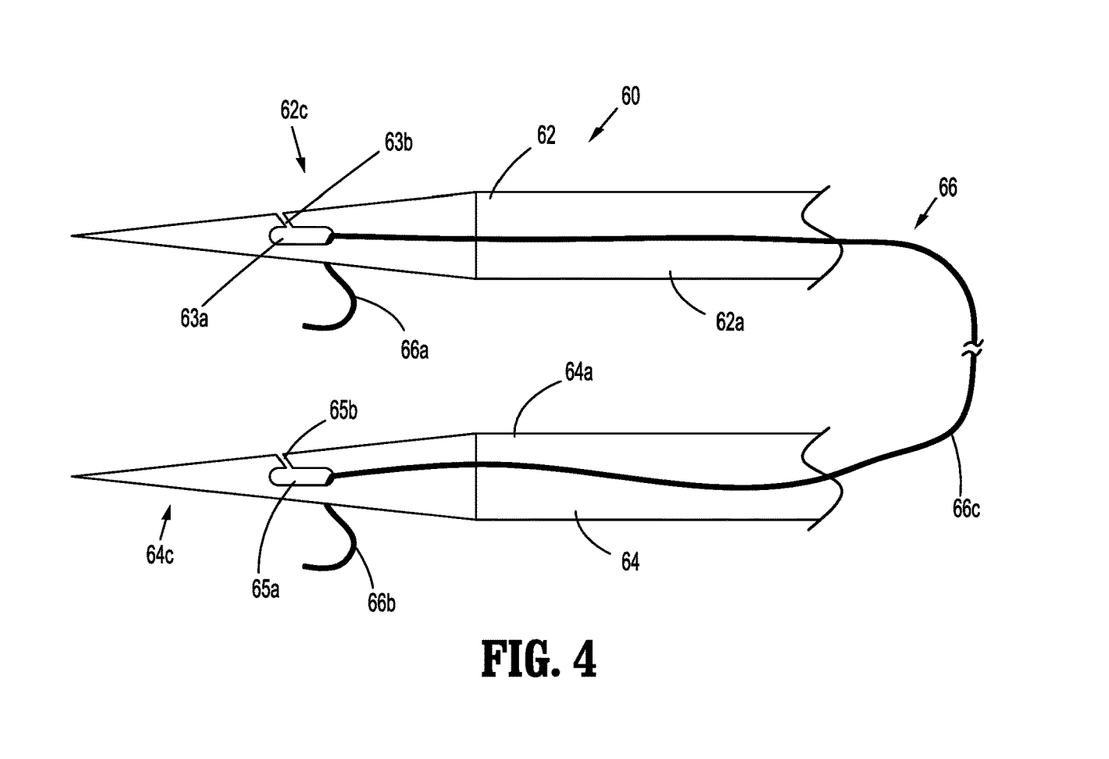
FIG. 4 is a side view of a needle assembly of the end effector of FIGS. 1-3.
Figure 5:
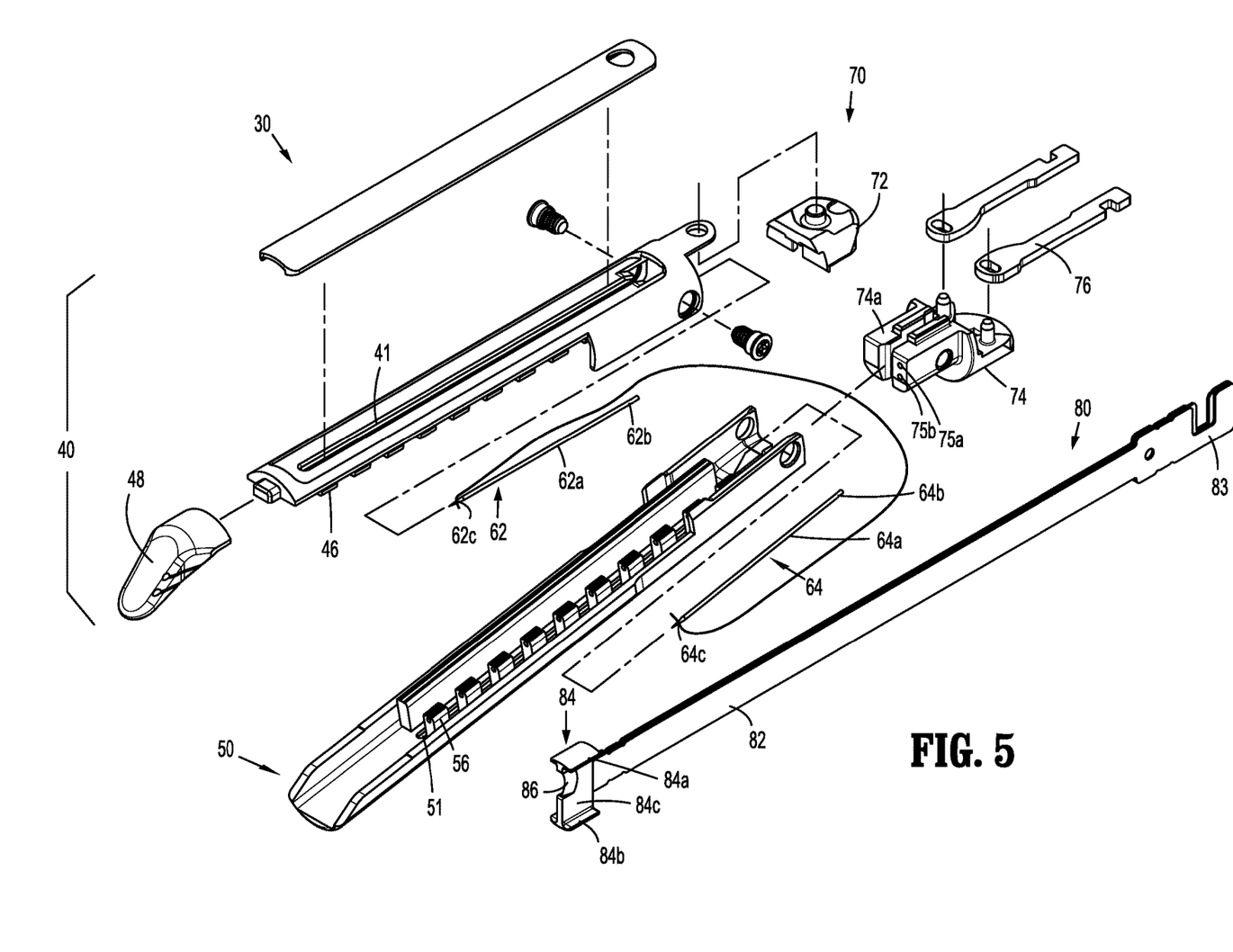
FIG. 5 is an exploded, perspective view of the jaw assembly of FIGS. 1-3.

As shown in FIGS. 4 and 5, a needle assembly 60 is slidably disposed within the end effector 30. The needle assembly 60 includes first and second needles 62, 64 configured and dimensioned to move through the needle channels 47a, 57a of the teeth 46, 56 of the first and second jaws 40, 50, respectively. Each of the first and second needles 62, 64 includes an elongate body 62a, 64a including a proximal end portion 62b, 64b operably coupled to a needle pusher 13 (FIG. 8B) of the handle assembly 10 for effecting longitudinal movement of the first and second needles 62, 64, and a sharp distal tip portion 62c, 64c for piercing tissue.

The distal tip portions 62c, 64c of the first and second needles 62, 64 each include a transverse hole 63a, 65a defined therethrough, and a passageway 63b, 65b extending between the transverse hole 63a, 65a and an outer surface of the needle 62, 64. A suture 66 is coupled to or threaded in the distal tip portions 62c, 64c of the first and second needles 62, 64. A first end portion 66a of the suture 66 is passed through the transverse hole 63a of the first needle 62 and a second end portion 66b of the suture 66 is passed through the transverse hole 65a of the second needle 64 such that a central portion 66c of the suture 66, which is disposed between the first and second end portions 66a, 66b, is free and extends proximally along the first and second needles 62, 64 (e.g., disposed within a proximal portion of the jaw assembly 34).

The first and second needles 62, 64 and the suture 66 are formed from biocompatible materials which are bioabsorbable or non-absorbable, natural or synthetic, or combinations thereof. The first and second needles 62, 64 may be straight needles formed from a surgical grade metal, and/or the suture 66 may be a monofilament suture formed from a non-absorbable material. It should be understood, however, that the materials and configuration of the first and second needles 62, 64 and the suture 66 may vary.

With continued reference to FIG. 5, in conjunction with FIG. 1, the end effector 30 includes a mounting assembly 70 pivotably coupling the proximal body portion 32 to the jaw assembly 34. The mounting assembly 70 includes an upper mounting member 72 and a lower mounting member 74. The upper mounting member 72 is fixedly secured to the lower mounting member 74 and the first jaw 40, and the lower mounting member 74 is pivotally secured to the second jaw 50. Coupling members 76 extend distally from the lower mounting member 74 for rotatably securing the mounting assembly 70 to the proximal body portion 32 of the end effector 30.

The lower mounting member 74 includes a pair of extensions 74a extending proximally into the second jaw 50. One extension of the pair of extensions 74a includes an upper or first opening 75a and a lower or second opening 75b extending longitudinally therethrough. The first and second openings 75a, 75b are aligned with the needle channels 47a, 57a of the first and second jaws 40, 50, respectively, when the first and second jaws 40, 50 are disposed in the closed position. The first and second openings 75a, 75b are configured and dimensioned for slidable passage of the first and second needles 62, 64 therethrough. Accordingly, the first and second needles 62, 64 can travel, respectively, through the first and second openings 75a, 75b of the mounting assembly 70 and into the needle channels 47a, 57a of the teeth 46, 56 of the respective first and second jaws 40, 50, to suture tissue disposed therebetween.

The end effector 30 further includes a drive assembly 80 operably associated with and slidably disposed between the first and second jaws 40, 50 of the jaw assembly 34. The drive assembly 80 includes an elongated drive beam 82 having a connector 83 at a proximal end thereof that is configured to releasably engage a drive member or firing rod 11 (FIG. 8B) of the handle assembly 10, and an I-beam 84 at a distal end thereof. The I-beam 84 includes an upper or first beam 84a, a lower or second beam 84b, and a vertical strut 84c interconnecting the first and second beams 84a, 84b. A knife 86 is formed on a distal face of the vertical strut 84c. The first and second beams 84a, 84b of the I-beam 84 can travel along the first and second jaws 40, 50 to move the first and second jaws 40, 50 to the closed position while the knife 86 travels between the elongated rails 44, 54 and the teeth 46, 56 of the respective tissue facing surfaces 42, 52, to longitudinally cut tissue disposed therebetween.

Figure 6:
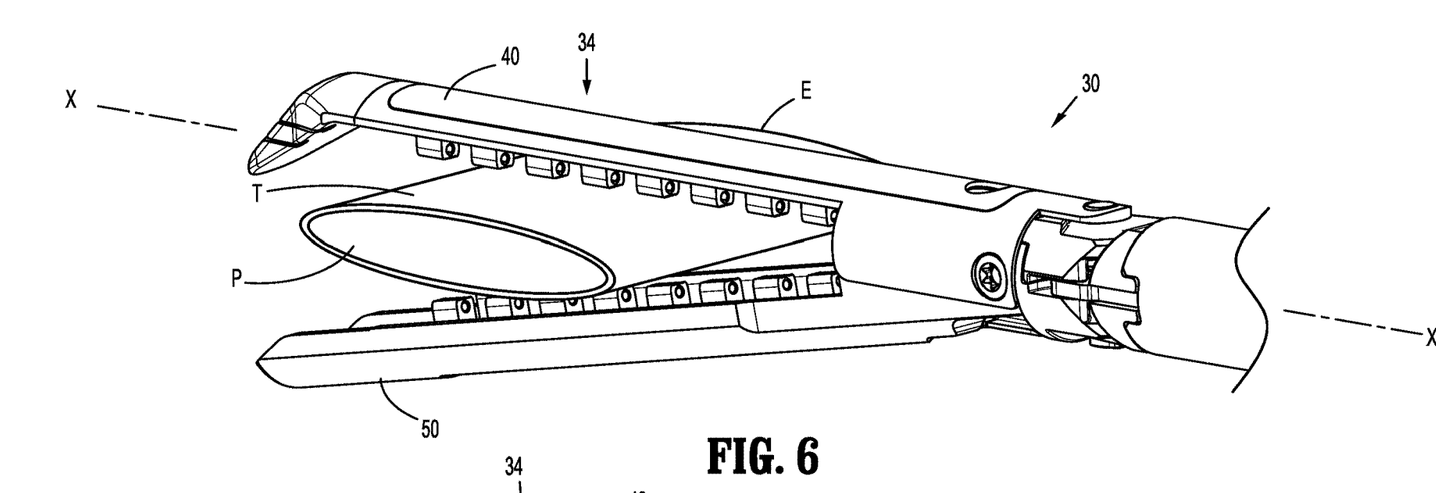
FIG. 6 is a side, perspective view of a jaw assembly of an end effector of the surgical suturing device of FIG. 1, shown in an open position with tissue positioned between first and second jaws of the jaw assembly during a surgical suturing procedure in accordance with an embodiment of the present disclosure.

To use the surgical suturing device 1, the end effector 30, which is loaded with the needle assembly 60 and secured to the distal end of the elongate body portion 20, is inserted through an access device (not shown), such as a trocar, a cannula, or an access port, and positioned at a desired surgical site. Tissue "T" is placed between the first and second jaws 40, 50 of the end effector 30, as shown in FIG. 6, with an opening "P" defined through the tissue "T" positioned substantially perpendicular to the central longitudinal axis "X" of the end effector 30 and the open end "E" of the tissue "T" extending laterally adjacent to the side of the end effector 30 including the elongated rails 44, 54 (FIG. 3). Once properly oriented and positioned, the jaw assembly 34 is moved from the open position, shown in FIG. 6, to the closed position, shown in FIG. 7, to clamp the tissue "T" between the first and second jaws 40, 50.

In the closed position, the elongated rails 44, 54 of the first and second jaws 40, 50 grip the tissue "T" to prevent slippage of the tissue "T" from the jaw assembly 34 and to uniformly compress the opening "P" in the tissue "T" closed. The portion of the tissue "T" disposed between the teeth 46, 56 of the first and second jaws 40, 50 take on a wave-like configuration including tissue portions "T1" compressed together between the tissue engaging surfaces 46a, 56a of the teeth 46, 56 and tissue portions "T2" spread apart (e.g., bulging, protruding, etc.) and bowed into the space defined between adjacent teeth 46, 56.

Figure 8A:
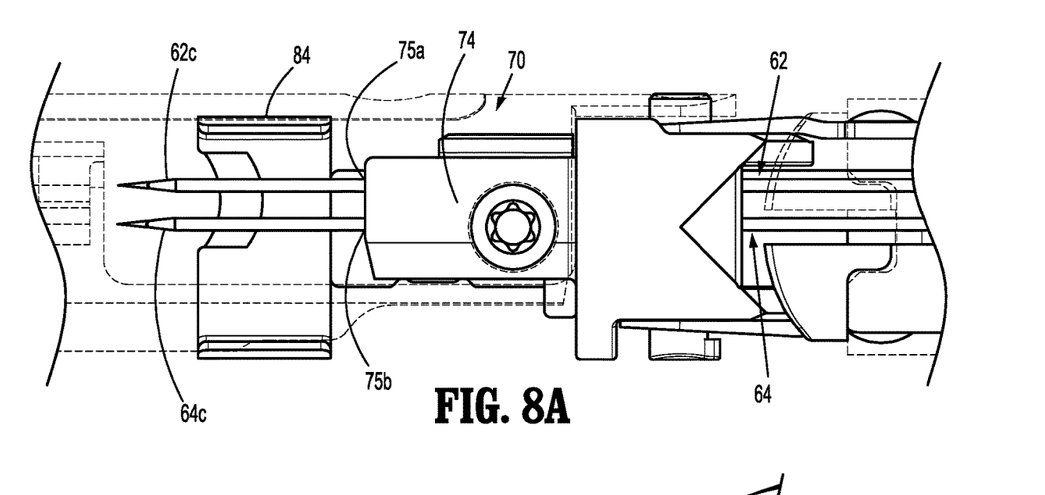
FIG. 8A is a side, close-up view of the end effector of FIG. 7, showing the first and second jaws in phantom, and illustrating distal portions of a needle assembly and a drive assembly of the end effector, prior to firing the surgical suturing device.
Figure 8B:
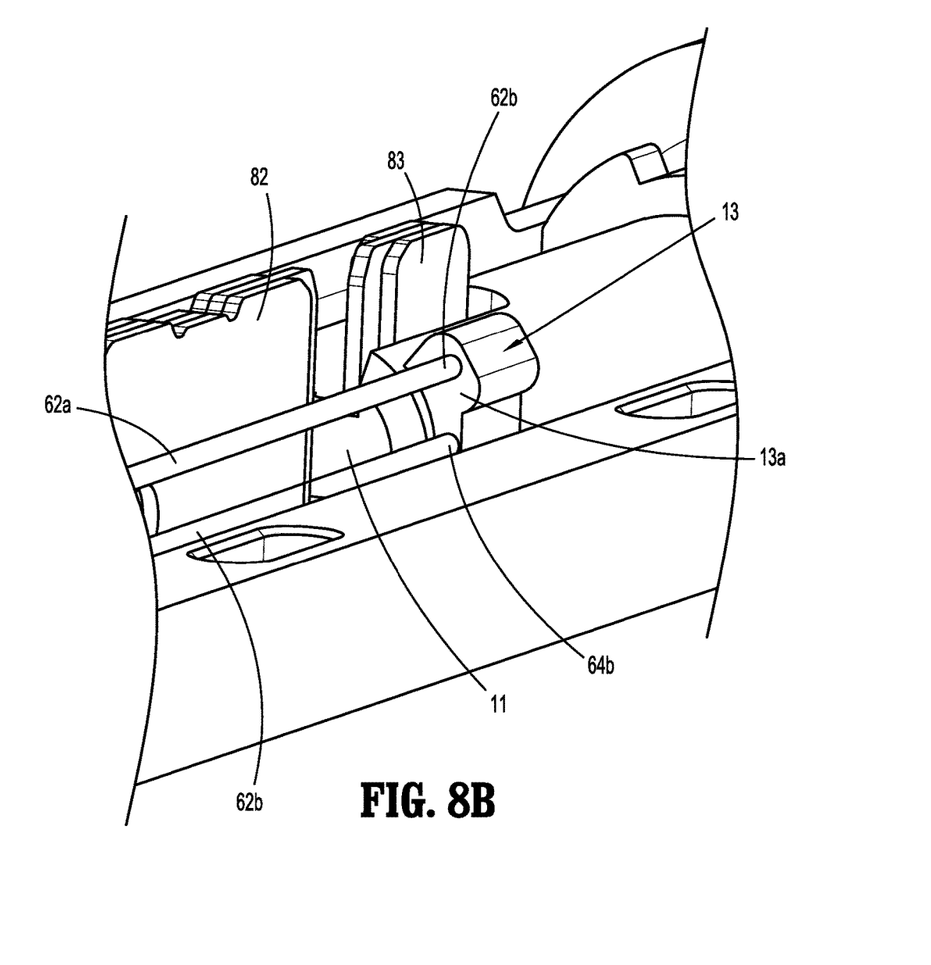
FIG. 8B is a side, close-up view of the end effector of FIG. 7, illustrating proximal portions of a needle assembly and a drive assembly of the end effector prior to firing the surgical suturing device.

The surgical suturing device 1 is then fired by actuating the trigger 12b of the handle assembly 10. In firing the surgical suturing device 1, the needle assembly 60 as well as the drive assembly 80 of the end effector 30 are advanced distally through the jaw assembly 34 from a first or retracted position to a second or advanced position. Specifically, as shown in FIGS. 8A and 8B, in the retracted position, the elongate bodies 62a, 64a of the first and second needles 62, 64 of the needle assembly 60 extend through the first and second openings 75a, 75b, respectively, of the mounting assembly 70 with the proximal end portions 62b, 64b abutting a distal face 13a of the needle pusher 13 and the distal tip portions 62c, 64c disposed proximal of the teeth 46, 56 of the first and second jaws 40, 50.

Figure 9A:
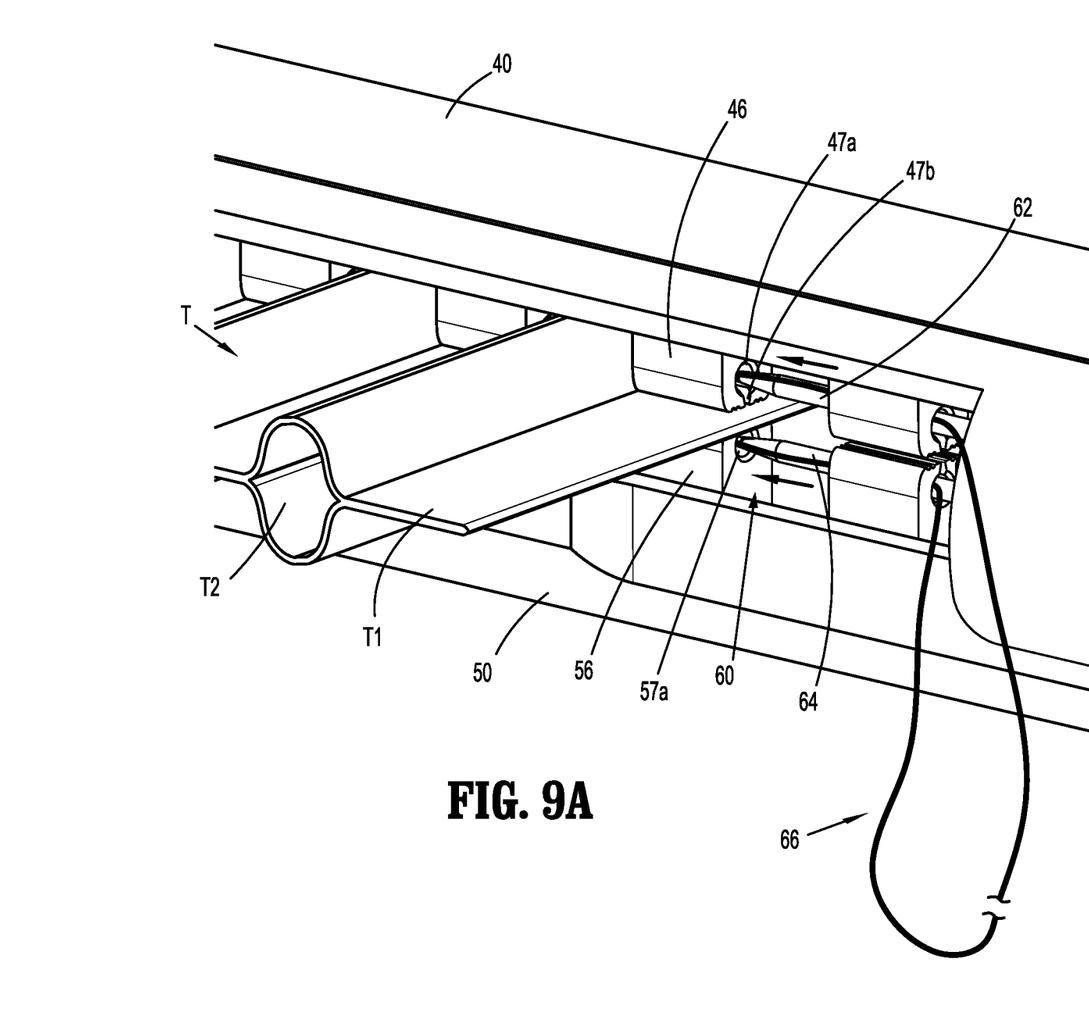
FIG. 9A is a side, close-up view of the end effector and the tissue of FIG. 7, during actuation of a firing stroke of the surgical suturing device.
Figure 9B:
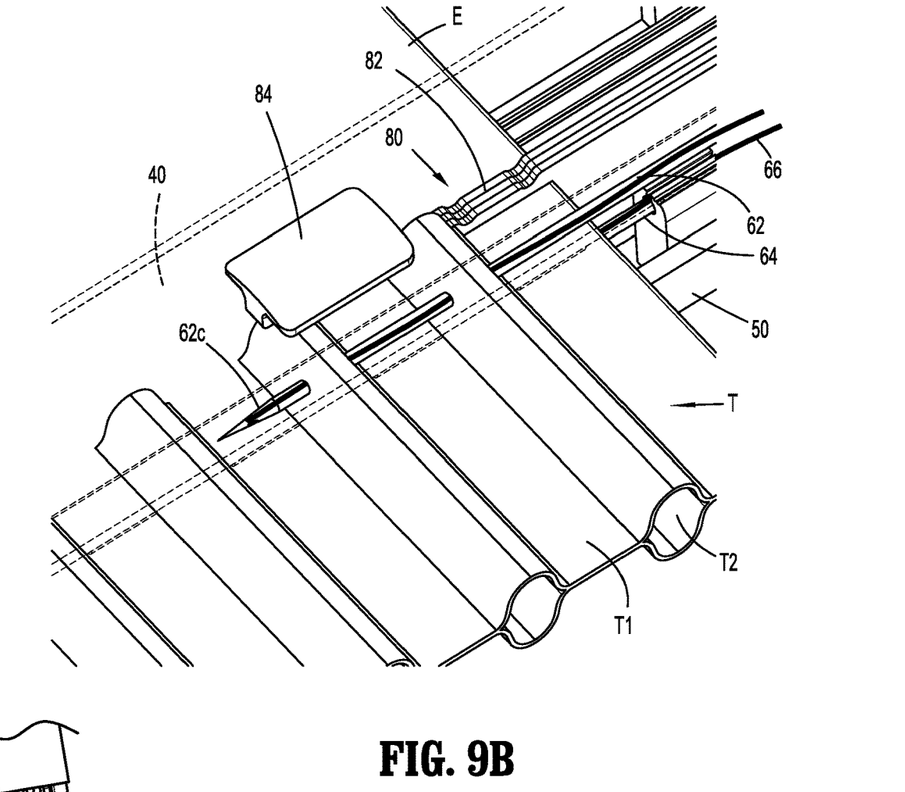
FIG. 9B is a top, close-up view of the end effector and the tissue of FIG. 7, showing the first jaw in phantom, during actuation of a firing stroke the surgical suturing device.

During the firing stroke, the firing rod 11, which is secured to the elongated drive beam 82 at the connector 83, and the needle pusher 13, which is secured (e.g., welded) to and extends laterally from the firing rod 11, are advanced distally to drive or push the elongated drive beam 82 and the first and second needles 62, 64 distally. As shown in FIG. 9A, the first and second needles 62, 64 pass, respectively, through the needle channels 47a, 57a of the teeth 46, 56 and through the tissue portions "T2" disposed in the space between adjacent teeth 46, 56. As the suture 66 is coupled to the first and second needles 62, 64, as discussed above, the suture 66 is also passed through the needle channels 47a, 57a of the teeth 46, 56 and the tissue portions "T2" disposed between the teeth 46, 56. The firm grasp of the tissue engaging surfaces 46a, 56a of the teeth 46, 56 on the tissue "T" allows the needle assembly 60 to penetrate and stitch the tissue portions "T2" disposed between the teeth 46, 56. Further, as shown in FIG. 9B, the elongated drive beam 82 of the drive assembly 80 passes through the central longitudinal slots 41, 51 (FIG. 5) of the first and second jaws 40, 50 with the knife 86 (FIG. 5) cutting (e.g., trimming) the tissue "T" immediately before suturing. It should be understood that the relative positioning of the knife 86 and the distal tip portions 62c, 64c of the first and second needles 62, 64 may be adjusted so that the cutting and suturing operations occur substantially simultaneously, or the tissue "T" is sutured and then cut. The firm grasp of the elongated rails 44, 54 on the tissue "T" allows the knife 86 to evenly cut the end "E" of the tissue "T."

The needle assembly 60 and the drive assembly 80 are advanced distally through the full firing stroke of the trigger 12b such that at the end of the firing stroke, the distal tip portions 62c, 64c of the first and second needles 62, 64 pass through the respective first and second apertures 49a, 49b of the tip portion 48 of the first jaw 40, as shown in FIG. 10. With the distal tip portions 62c, 64c of the first and second needles 62, 64 extending distally of the first jaw 40, the first and second end portions 66a, 66b of the suture 66 are grasped by grasping instruments 2. The needle assembly 60 and the drive assembly 80 are then retracted proximally and the first and second jaws 40, 50 are opened (e.g., via the retraction knob 19 of the handle assembly 10) so that the surgical suturing device 1 can be removed from the now sutured tissue "T." The needle pusher 13 may include apertures (not explicitly shown) disposed in the distal face 13a thereof that frictionally and yet releasably engage the proximal end portions 62b, 64b of the first and second needles 62, 64 such that when the firing rod 13 is retracted proximally, the first and second needles 62, 64 are also retracted proximally, and when the end effector 30 is detached from the handle assembly 10, the needle pusher 13 releases the first and second needles 62, 64.

Figure 11:
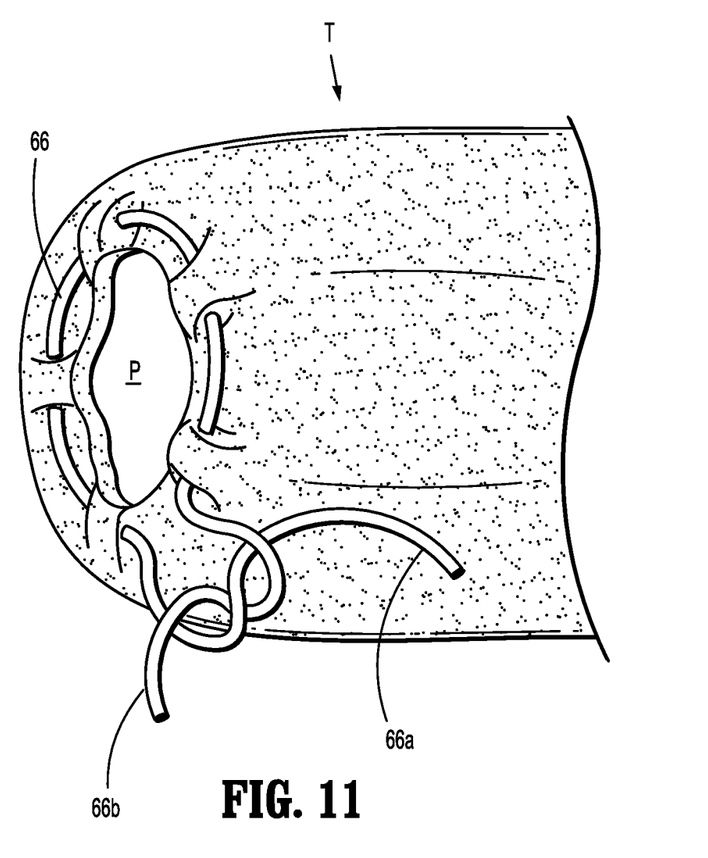
FIG. 11 is a side, perspective view of the tissue of FIGS. 6-10 after performing the surgical suturing procedure.

As the first and second end portions 66a, 66b of the suture 66 are held by the grasping instruments 2, during retraction of the first and second needles 62, 64, the suture 66 passes through the passageways 63b, 65b of the first and second needles 62, 64 so that only the first and second needles 62, 64 are retracted and the suture 66 is retained in the needle channels 47a, 57a of the teeth 46, 56 of the first and second jaws 40, 50, as well as through the tissue "T" disposed between adjacent teeth 46, 56. Accordingly, when the first and second jaws 40, 50 are opened to release the tissue "T," the suture 66 is freed from the jaw assembly 34 by passing through the slits 47b, 57b of the teeth 46, 56 as well as the open side of the tip portion 48, leaving the suture 66 attached to the tissue "T" around the perimeter thereof, as shown in FIG. 11. The first and second end portions 66a, 66b of the suture 66 are then pulled to tighten the suture 66 and narrow the opening "P" defined in the tissue "T," such as around an anvil or cartridge assembly (not shown) of a circular stapler.

While the end effector 30 is shown as including a drive assembly 80 having a knife 86, it should be understood that the drive assembly 80 may be modified to omit the knife 86 such that the surgical suturing device 1 does not cut tissue.

The end effector 30 of the present disclosure may be a single use end effector 30 that is pre-loaded with the needle assembly 60, with or without the suture 66, during manufacture of the end effector 30. Alternatively, the end effector 30 may be reusable. The first and second needles 62, 64 of the needle assembly 60 may be a fixed, permanent component of the end effector 30 or an interchangeable, releasably engaged part thereof, and/or the suture 66 may be a replaceable component of the end effector 30.

The end effectors 30 described herein may also be configured for use with other surgical apparatus, such as electromechanical surgical devices as described, for example, in U.S. Patent Appl. Pub. Nos. 2015/0157320 and 2015/0157321, the entire contents of each of which are incorporated herein by reference.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical suturing device comprising:
   an end effector including:
      a jaw assembly including a first jaw and a second jaw, the first and second jaws movable between an open position and a closed position, each of the first and second jaws including a tissue facing surface having an elongated rail and a longitudinal row of teeth, each of the elongated rails having a tissue clamping surface, the tissue clamping surfaces configured to grasp tissue therebetween when the first and second jaws are in the closed position, each tooth of the longitudinal rows of teeth of the first and second jaws including a needle channel extending therethrough, the elongated rails and the longitudinal rows of teeth of the first and second jaws disposed in opposed relation relative to each other; and a needle assembly including a first needle, a second needle, and a suture coupled to the first and second needles, the first needle slidable through the needle channels of the longitudinal row of teeth of the first jaw and the second needle slidable through the needle channels of the longitudinal row of teeth of the second jaw.

2. The surgical suturing device according to claim 1, wherein each of the tissue facing surfaces of the first and second jaws includes a central longitudinal slot defined therein.

3. The surgical suturing device according to claim 2, wherein the elongate rail and the longitudinal row of teeth of each of the first and second jaws are disposed on opposed sides of the central longitudinal slot of the respective first or second jaw.

4. The surgical suturing device according to claim 2, wherein the end effector further includes a drive assembly including an elongated drive beam and a knife, the knife movable through the central longitudinal slots of the first and second jaws.

5. The surgical suturing device according to claim 1, wherein each tooth of the longitudinal rows of teeth of the first and second jaws has a tissue engaging surface, the tissue engaging surfaces configured to grasp tissue therebetween when the first and second jaws are in the closed position.

6. The surgical suturing device according to claim 1, wherein each tooth of the longitudinal rows of teeth of the first and second jaws has a slit defined therein that extends between the needle channel and an outer surface of the tooth.

7. The surgical suturing device according to claim 1, wherein the first jaw includes a tip portion having first and second apertures extending therethrough, the first aperture aligned with the needle channels of the first jaw and the second aperture aligned with the needle channels of the second jaw when the first and second jaws are in the closed position.

8. The surgical suturing device according to claim 7, wherein each of the first and second apertures of the tip portion are defined by a semi-continuous surface such that the first and second apertures are open at an outer side surface of the tip portion.

9. The surgical suturing device according to claim 1, wherein each of the first and second needles of the needle assembly includes a distal tip portion having a transverse hole extending therethrough, and a first end portion of the suture extends through the transverse hole of the first needle and a second end portion of the suture extends through the transverse hole of the second needle.

10. The surgical suturing device according to claim 9, wherein each of the first and second needles includes a passageway extending between the transverse hole and an outer surface of the respective first or second needle.

11. The surgical suturing device according to claim 1, wherein the end effector further includes a proximal body portion and a mounting assembly pivotably coupling the proximal body portion to the jaw assembly, the mounting assembly including first and second openings extending longitudinally therethrough, the first and second openings aligned with the needle channels of the first and second jaws when the first and second jaws are in the closed position and configured for passage of the first and second needles therethrough.

12. The surgical suturing device according to 1, further including a handle assembly and an elongate body portion extending distally from the handle assembly, the end effector extending distally from the elongate body portion.

13. A method of securing a purse string suture to tissue, the method comprising:

positioning tissue between tissue facing surfaces of first and second jaws of an end effector of a surgical suturing device, each of the tissue facing surfaces of the first and second jaws including an elongated rail and a longitudinal row of teeth, each tooth of the longitudinal rows of teeth including a needle channel extending therethrough;

closing the first and second jaws such that the tissue is clamped between the elongated rails of the first and second jaws and takes on a wave-like configuration between the longitudinal rows of teeth, the wave-like configuration including first tissue portions compressed together between opposed teeth of the longitudinal rows of teeth and second tissue portions spread apart and bowed into the spaces defined between adjacent teeth of each of the longitudinal rows of teeth; and actuating the surgical suturing device to advance a needle assembly of the end effector distally through the jaw assembly to suture the tissue disposed therebetween, the needle assembly including a suture coupled to first and second needles, the first and second needles slidable through the needle channels of the longitudinal rows of teeth of the first and second jaws and the tissue disposed in the spaces between adjacent teeth of the longitudinal rows of teeth, and to advance a drive assembly of the end effector distally through the jaw assembly to cut the tissue disposed between the first and second jaws.

14. The method according to claim 13, wherein actuating the surgical suturing device includes advancing distal tip portions of the first and second needles through first and second apertures defined in a tip portion of the first jaw.

15. The method according to claim 14, further including grasping first and second end portions of the suture with grasping instruments.

16. The method according to claim 15, further including retracting the needle assembly proximally into a proximal body portion of the end effector and opening the first and second jaws such that the suture passes through slits defined in each tooth of the longitudinal rows of teeth as well as an open side of the tip portion, leaving the suture attached to the tissue around a perimeter thereof.

17. A surgical suturing device comprising:
an end effector including:
a jaw assembly including a first jaw and a second jaw, the first and second jaws movable between an open position and a closed position, each of the first and second jaws including a tissue facing surface having an elongated rail, a longitudinal row of teeth, and a central longitudinal slot defined therein, each tooth of the longitudinal rows of teeth of the first and second jaws including a needle channel extending therethrough, the elongated rails and the longitudinal rows of teeth of the first and second jaws disposed in opposed relation relative to each other;

a needle assembly including a first needle, a second needle, and a suture coupled to the first and second needles, the first needle slidable through the needle channels of the longitudinal row of teeth of the first jaw and the second needle slidable through the needle channels of the longitudinal row of teeth of the second jaw; and a drive assembly including an elongated drive beam and a knife, the knife movable through the central longitudinal slots of the first and second jaws.

18. The surgical suturing device according to claim 17, wherein each tooth of the longitudinal rows of teeth of the first and second jaws has a slit defined therein that extends between the needle channel and an outer surface of the tooth.

19. The surgical suturing device according to claim 17, wherein the first jaw includes a tip portion having first and second apertures extending therethrough, the first aperture aligned with the needle channels of the first jaw and the second aperture aligned with the needle channels of the second jaw when the first and second jaws are in the closed position.

20. The surgical suturing device according to claim 17, wherein each of the first and second needles of the needle assembly includes a distal tip portion having a transverse hole extending therethrough, and a first end portion of the suture extends through the transverse hole of the first needle and a second end portion of the suture extends through the transverse hole of the second needle.

\* \* \* \* \*